(12) United States Patent
Lemmon (10) Patent No.: US 7,637,943 B2
(45) Date of Patent: Dec. 29, 2009

(54) PROSTHETIC HEART VALVE SIZER ASSEMBLY WITH FLEXIBLE SIZER BODY

(75) Inventor: Jack D. Lemmon, St. Louis Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 55 days.

(21) Appl. No.: 11/842,636

(22) Filed: Aug. 21, 2007

(65) Prior Publication Data

US 2008/0033544 A1 Feb. 7, 2008

Related U.S. Application Data

(62) Division of application No. 10/688,718, filed on Oct. 17, 2003, now Pat. No. 7,258,698.

(51) Int. Cl.
*A61F 2/24* (2006.01)

(52) U.S. Cl. .................................................. 623/2.11

(58) Field of Classification Search ....... 623/2.11–2.42; 606/102
See application file for complete search history.

(56) References Cited

U.S. PATENT DOCUMENTS

| 5,360,014 | A | 11/1994 | Sauter et al. |
|---|---|---|---|
| 5,814,096 | A | 9/1998 | Lam et al. |
| 6,350,281 | B1 | 2/2002 | Rhee |
| 6,582,419 | B1 | 6/2003 | Schoon et al. |
| 2002/0020074 | A1 | 2/2002 | Love et al. |
| 2002/0173842 | A1 | 11/2002 | Buchanan |
| 2004/0024451 | A1 | 2/2004 | Johnson et al. |

*Primary Examiner*—Bruce E Snow
(74) *Attorney, Agent, or Firm*—Mike Jaro; Jeffrey J. Hohenshell (57) ABSTRACT

A method for evaluating a valve annulus to determine a size of a prosthetic heart valve to be sewn to the valve annulus during heart valve replacement surgery. The prosthetic heart valve includes an annular extension having a first flexibility and a sewing ring having a second flexibility. A flexible sizer body is provided and includes an outer ring and an annular wall coupled to and extending from the outer ring. The annular wall has a flexibility substantially similar to the first flexibility of the annular extension of the prosthetic heart valve. The flexible sizer body is inserted into the valve annulus and a determination made as to fit and conformance. A prosthetic heart valve is selected based on the determination.

16 Claims, 8 Drawing Sheets

PROSTHETIC HEART VALVE SIZER ASSEMBLY WITH FLEXIBLE SIZER BODY

CROSS-REFERENCE TO RELATED APPLICATIONS

This application is a divisional of U.S. patent application Ser. No. 10/688,718, filed Oct. 17, 2003, now U.S. Pat. No. 7,258,698, and entitled "Prosthetic Heart Valve Sizer Assembly with Flexible Sizer Body;" the entire teachings of which are incorporated herein by reference.

BACKGROUND

The present disclosure relates to a sizer for implantable prosthetic heart valves. More particularly, the present disclosure relates to a sizer for more precisely determining the proper size of a prosthetic heart valve to be implanted during heart valve replacement surgery.

Various types and configurations of prosthetic heart valves, used to replace diseased natural human heart valves, are known in the art. The actual shape and configuration of any particular prosthetic heart valve is, of course, dependent to some extent upon the valve being replaced (i.e., mitral valve, tricuspid valve, aortic valve, and pulmonary valve). In general terms, however, the prosthetic heart valve design attempts to replicate the function of the valve being replaced and thus will include valve leaflet like structures. With this in mind, prosthetic heart valves including valve leaflets are generally categorized as either forming relatively flexible leaflets or relatively rigid leaflets.

The category including prosthetic heart valves which form relatively flexible leaflets includes bioprosthetic heart valves having leaflets made of a biological material as well as prosthetic heart valves having leaflets made of synthetic (e.g., polymeric) material. Flexible leaflet prosthetic heart valves are generally categorized as having a frame or stent or as having no stent. The stent in a stented prosthetic heart valve normally includes a substantially circular base or stent ring around which an annular suture material is disposed for suturing the prosthesis to heart tissue. The stent ring including the annular suture material is typically referred to as a sewing ring. Further, the stent forms at least two, typically three, support structures extending from a stent ring. The support structures are commonly referred to as stent posts or commissure posts and include an internal, rigid yet flexible structure extending from the stent ring, covered by a cloth-like material similar to that of the annular suture material. The stent or commissure posts define the junction between adjacent tissue or synthetic leaflets otherwise secured there too.

Examples of prosthetic heart valves are described in U.S. Pat. No. 4,106,129 to Carpentier et al. and U.S. Pat. No. 5,037,434 to Lane, the teachings of which are incorporated herein by reference. These disclosures detail a conventional configuration of three leaflets wherein one leaflet is disposed between each pair of stent or commissure posts. The Hancock® Modified Orifice Aortic Bioprosthesis and the Hancock® II Bioprosthesis, both manufactured by Medtronic, Inc., Minneapolis, Minn., are commercially available examples of bioprosthetic valves. Both the Hancock® Modified Orifice Bioprosthesis and the Hancock® II are available in various sizes such that they may be implanted in patients having corresponding varying sizes of heart valve annuli.

Prosthetic heart valves categorized as forming relatively rigidly leaflets include mechanical prosthetic heart valves. A typical mechanical heart valve includes an annular valve housing or body to provide a passageway for blood flow. Relatively rigid leaflets are rotatably mounted to the annular housing and rotate to open or close the blood flow passageway. The Medtronic Hall® mechanical heart valve, manufactured by Medtronic, Inc., Minneapolis, Minn., is a commercially available example of a mechanical heart valve. Similar to bioprosthetic valves, mechanical heart valves are available in various sizes such that they may be implanted in patients having corresponding varying sizes of heart valve annuli.

During valve replacement surgery, the heart valve prosthesis, whether it be a bioprosthesis or a mechanical heart valve, is implanted within the patient's heart either in a supra-annular or intra-annular implant technique. The supra-annular implant technique sutures the prosthetic heart valve above the annulus corresponding to the heart valve to be replaced. The intra-annular implant technique sutures the prosthetic heart valve within the annulus corresponding to the heart valve to be replaced.

Ideally, the heart valve annulus is formed of relatively healthy tissue receptive to some shaping by the surgeon in preparation of receiving the heart valve prosthesis. However, due in part to the space and time constraints during valve replacement surgery, the shape of the resulting annulus is often less than perfect for the attachment of a heart valve prosthesis. At times, the annulus and/or the patient's natural leaflets are calcified, requiring complete annular debridement or removal of the hardened tissue. The annular debridement results in a less defined annulus ledge and larger overall orifice into which, or above which, the prosthetic heart valve is to be attached. As such, the size and contour of each annulus varies widely from patient to patient.

Due to the uneven nature of the annuli, it is crucial that a surgeon select a properly sized prosthetic heart valve to match a particular patient's annulus. Typical annulus sizers are simple cylinders made out of rigid plastics, wherein the cylinder diameter corresponds to a size of a particular prosthetic heart valve. During surgery, a surgeon typically has a number of sizers at his or her disposal, each sizer having a different size or diameter (i.e., each sizer relating to a different size of prosthetic heart valve). A surgeon inserts the sizer or a series of different sizers into the valve opening to measure the size of the valve opening. Upon determining the size of the valve opening, the surgeon selects a heart valve prosthesis for implantation having a size believed to correspond to the size of the valve opening.

Although typical annulus sizers are rigid, the sewing or attachment ring included on prosthetic heart valves are flexible. When inserted within or above the valve annulus, the sewing ring compresses and conforms more closely to the heart valve annulus. Where the selected heart valve prosthesis has a diameter substantially identical to the rigid sizer otherwise found to best "match" the annulus, this compression or conformity may result in the selected prosthetic heart valve being too small for the valve opening or annulus. Other times, a heart valve prosthetic sized to fit the valve opening may be too large for attachment to an unusually small annulus ledge. Accordingly, typical prosthetic heart valve sizers often erroneously suggest the size of prosthetic heart valve to be implanted. In such a case, the selected prosthetic heart valve is discarded and a new prosthetic heart valve is chosen. Not only is this a waste of the relatively expensive valve prosthesis, but it is also a waste of time, which is often critical to the patient's well being in valve replacement surgery. Therefore, in light of the above, a need exists for a prosthetic heart valve sizer that more accurately represents the actual size and flexibility of the prosthetic heart valve to be implanted.

SUMMARY

An aspect of the present disclosure relates to a flexible sizer body for evaluating a valve annulus to determine a size of a prosthetic heart valve to be sewn to the valve annulus during heart valve replacement surgery. The prosthetic heart valve includes an annular extension having a first flexibility and a sewing ring having a second flexibility. The flexible sizer body includes an outer ring and an annular wall coupled to and extending from the outer ring. The annular wall has a flexibility substantially similar to the first flexibility of the annular extension of the prosthetic heart valve.

Another aspect of the present disclosure relates to a sizer for evaluating a valve annulus to determine a size of a prosthetic heart valve to be sewn to the valve annulus during heart valve replacement surgery. The prosthetic heart valve including an annular extension having a first flexibility and a sewing ring having a second flexibility. The sizer includes a handle defining a first end and a second end, and a flexible sizer body coupled with the first end of the handle. The flexible sizer body includes an outer ring and an annular wall coupled to and extending from the outer ring. The annular wall has a flexibility that approximates the flexibility of the annular extension of the prosthetic heart valve.

Another aspect of the present disclosure relates to a method for evaluating a valve annulus to determine a proper size of a prosthetic heart valve to be sewn to the valve annulus during heart valve replacement surgery. The prosthetic heart valve includes an annular extension having a first flexibility and a sewing ring having a second flexibility. The method includes providing a flexible sizer body, inserting the flexible sizer body into an opening of the heart valve annulus to determine whether the flexible sizer body properly fits and conforms with the heart valve annulus, and selecting the prosthetic heart valve to be sewn in the heart valve annulus based upon the determination of whether the flexible sizer body properly fit and conformed with the heart valve annulus. The flexible sizer body includes an outer ring and an annular wall. The annular wall is coupled to and extends from the outer ring. The annular wall has a flexibility that approximates the flexibility of the annular extension of the prosthetic heart valve.

DETAILED DESCRIPTION

Figure 1:
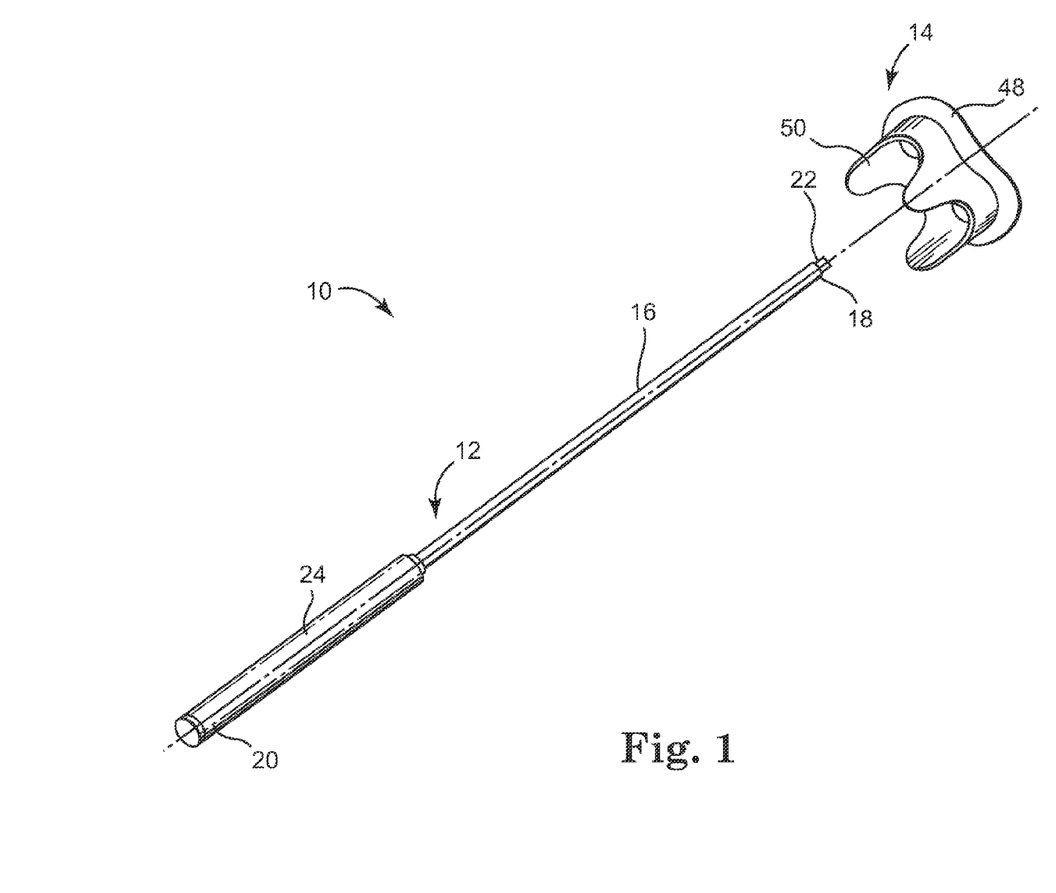
FIG. 1 is a perspective and exploded view of one embodiment of a prosthetic heart valve sizer assembly with a flexible sizer body in accordance with the present invention.

One preferred embodiment of a prosthetic heart valve sizer assembly 10 is illustrated in FIG. 1. The sizer assembly 10 generally includes a handle 12 and a flexible sizer body 14 coupled with the handle 12. The handle 12 includes a shaft or a rod 16 defining a distal end 18 opposite a proximal end 20 (generally indicated in FIG. 1). The handle 12 also defines a connector 22 on the distal end 18 to interface with and facilitate coupling of the sizer body 14 with the handle 12. In particular, the connector 22 is formed to facilitate a snap connection, a threaded connection, or any other spatially feasible and biocompatible, selective or permanent attachment to the sizer body 14.

The shaft 16 is formed of a bendable, biocompatible metal including but not limited to stainless steel or nitinol. Further, the handle 12 preferably includes a grip portion 24 near the proximal end 20 thereof to aid a surgeon (not shown) in grasping and manipulating the handle 12. The grip portion 24 has a larger dimension or diameter than the shaft 16 to facilitate ergonomic handling of the handle 12 by the surgeon. The grip portion 24 is preferably formed of a polymeric material to facilitate gripping of the handle 12. Alternatively, other constructions are equally acceptable, and the grip portion 24 can be eliminated entirely.

Figure 2A:
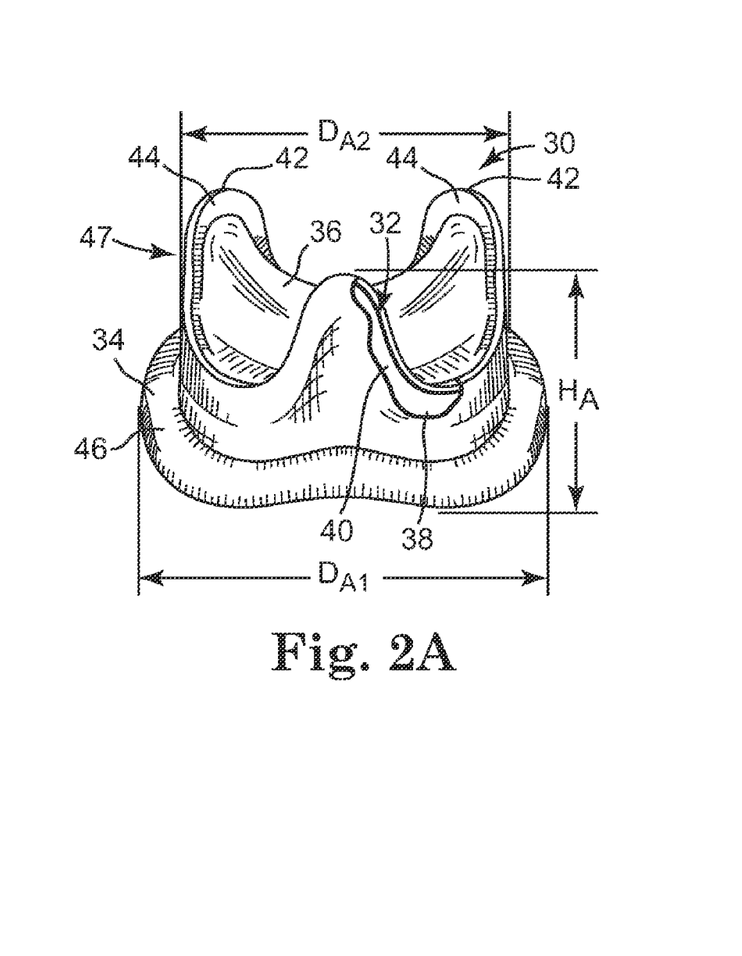
FIG. 2A is a perspective view of one embodiment of a bioprosthetic heart valve corresponding to the flexible sizer body illustrated in FIG. 1.

The sizer body 14, which is selectively coupled to the connector 22, is representative of a prosthetic heart valve, such as a bioprosthetic heart valve 30 illustrated in FIG. 2A. In general terms, the bioprosthetic heart valve 30 includes a stent 32, a sewing ring 34 and leaflets 36. As is known in the art, the stent 32 provides a support framework for the bioprosthetic heart valve 30. The stent 32 includes an inner frame member or stent ring 38, which typically defines a circular or parabolic ring, and stent posts 40.

Each of the stent posts 40 extends from the stent ring 38 and terminates in a rounded tip or free end 42 opposite the stent ring 38. As is known in the art, the internal structure of each of the stent posts 40 is formed as a stiff but resiliently bendable material. This construction allows the stent posts 40 to be inwardly defected from the orientation illustrated in FIG. 2A by an external force, such as an external force from an insertion handle to position the bioprosthetic heart valve 30, during use. Once this external force is removed, however, the stent posts 40 return to the original position illustrated in FIG. 2A. Finally, a cloth cover 44 is preferably formed over the stent ring 38 and the stent posts 40. The cover 44 is formed of a biocompatible, fabric material. In general, the stent 32 and the cover 44 form an annular extension 47.

The sewing ring 34 is coupled to and extends around the stent ring 38 opposite the stent posts 40. The sewing ring 34 serves as a flexible flange for subsequent suturing of the bioprosthetic heart valve 30 to a heart valve annulus. The sewing ring 34 preferably includes a cloth cover 46, similar to the cloth cover 44, to facilitate suturing of the sewing ring 34 to the stent 32 and the heart valve annulus.

Each of the leaflets 36 is sutured to the cloth cover 44. In particular, the leaflets 36 are sutured to the cloth cover 44 that covers the stent posts 40 such that each leaflet 36 extends between two of the stent posts 40. Each of the leaflets 36 is also sutured to the cloth cover 44 covering the stent ring 38 between the two stent posts 40. The leaflets 36 are made of biological or synthetic (e.g., polymeric) material and are configured to open and close to regulate blood flow when implanted.

Notably in view of the above description, the annular extension 47 has a first flexibility and the sewing ring 34 has a second flexibility. The first flexibility normally differs from the second flexibility. As such, the entire bioprosthetic heart valve 30 accordingly defines a variable flexibility. Further, it will be understood that the above described bioprosthetic heart valve 30 is but one acceptable configuration, for example, more or less than three of the stent posts 40 can be provided, the stent posts 40 may incorporate a different covering 44, and/or the covering 44 may be eliminated.

The bioprosthetic heart valve 30 is available in a plurality of sizes corresponding to the plurality of sizes of annuli found in heart valve replacement patients. In particular, the bioprosthetic heart valve 30 has a sewing ring maximum diameter $D_{A1}$ ranging from approximately 18 mm to 30 mm. The bioprosthetic heart valve 30 also has a maximum stent diameter $D_{A2}$, which is less than the sewing ring maximum diameter $D_{A1}$ and which ranges in sizes accordingly. An overall or maximum height $H_A$ also varies with differently sized bioprosthetic heart valves 30.

Figure 2B:
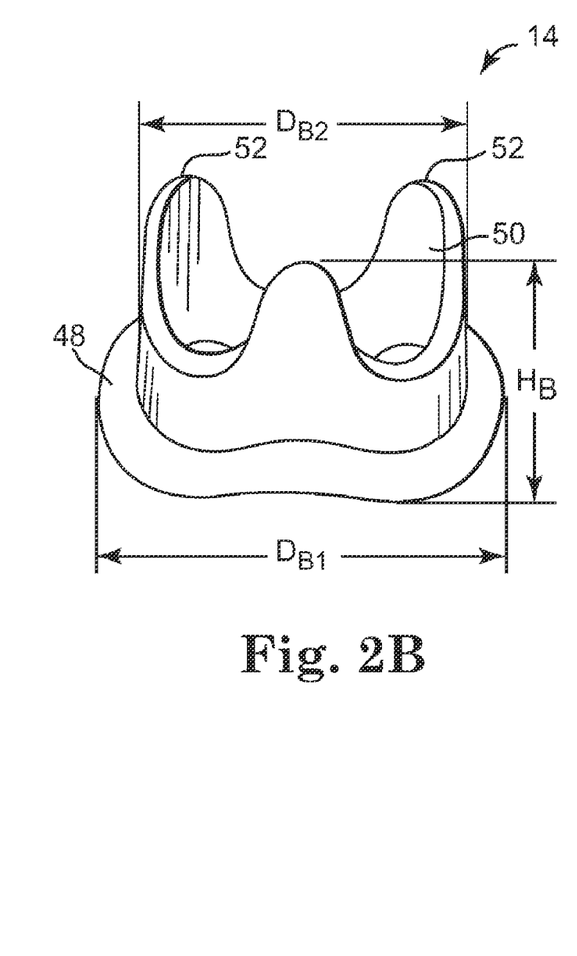
FIG. 2B is a perspective view of one embodiment of the flexible sizer body illustrated in FIG. 1.

With the above background in mind, one embodiment of the sizer body 14 of the sizer assembly 10 (FIG. 2) corresponding to the exemplary bioprosthetic heart valve 30 of FIG. 2A is illustrated in FIG. 2B. The sizer body 14 includes an outer ring 48 and an annular wall 50. The outer ring 48 is sized and shaped in a similar manner as the sewing ring 34 of the bioprosthetic heart valve 30. Accordingly, the outer ring 48 has a circular or parabolic shape and contour substantially similar to or matching the shape and contour of the sewing ring 34, such that each exposed dimension of the outer ring 48 is within 1 mm of the corresponding exposed dimension of the sewing ring 34. The outer ring 48 defines a maximum diameter $D_{B1}$ substantially equal to the maximum sewing ring diameter $D_{A1}$ of the bioprosthetic heart valve 30. Otherwise stated, the maximum diameter $D_{B1}$ is within 1 mm of the maximum sewing ring diameter $D_{A1}$. Furthermore, the outer ring 48 is formed with a flexibility representative of or approximating the flexibility of the sewing ring 34. Notably, a representative flexibility is a flexibility in which the outer ring 48 deforms or conforms to an area in a substantially similar manner under substantially similar external forces as the sewing ring 34 being represented. In other words, the outer ring 48 has a substantially similar flexibility as the sewing ring 34. Preferably, the outer ring 48 has a flexibility within 5% to 10% of the flexibility of the sewing ring 34. In one embodiment, the outer ring 48 has a flexibility in the range of 90 to 110% of the sewing ring 34. The representative flexibility of the outer ring 48 is achieved by varying material thickness of the outer ring 48, by varying a durometer of the material from the outer ring 48, or by forming the outer ring 48 to include a stiffening element within an over-molded elastomeric material as described below.

The annular wall 50 extends from the outer ring 48, in a similar manner, the stent posts 40 extend from the stent ring 38, terminating in rounded extremities or tips 52. The annular wall 50 is sized and shaped in a similar manner as the stent 32 of the bioprosthetic heart valve 30. Therefore, with the embodiment of FIG. 2B, the sizer body 14 representing the heart valve 30, which has three of the stent posts 40, will similarly form three of the rounded extremities 52. Alternatively, the annular wall 50 can form only two rounded extremities 52 to mimic a two stent post-type bioprosthetic heart valve (not shown). Each of the extremities are sized and spaced from one another similar to how the stent posts 40 and free ends 42 (FIG. 2A) are sized and spaced from one another. Accordingly, the annular wall 50 extends from the outer ring 48 to produce an overall height $H_B$ of the sizer body 14 substantially equal to the overall height $H_A$ of the bioprosthetic heart valve 30. Further, the annular wall 50 defines a maximum wall diameter $D_{B2}$ substantially equal to the maximum stent diameter $D_{A2}$. Otherwise stated, the height $H_B$ is within 1 mm of the height $H_A$, and the maximum wall diameter $D_{B2}$ is within 1 mm of the maximum stent diameter $D_{A2}$.

The annular wall 50 has a flexibility representative of or approximating the actual flexibility of the annular extension 47, i.e., the annular wall 50 has a flexibility similar to the flexibility of the annular extension 37. As such, the annular wall 50 is formed to be stiff but resiliently bendable so as to allow inward deflection of the rounded extremities 52 from the orientation shown in FIG. 2B upon application of an external force, such as the external force of a prosthetic valve holder. Once this external force is removed, however, the rounded extremities 52 return to the position illustrated in FIG. 2B. In an alternative embodiment, the sizer assembly 10 (FIG. 1) further includes a mechanism (not shown) for deflecting the rounded extremities 52 similar to typical prosthetic valve holders, such as the "Holder for Heart Valve" described in U.S. Pat. No. 5,476,510 to Eberhardt et al., the "Heart Valve System" described in U.S. Patent Publication No. 2003/0125805A1 of Johnson et al., or the "Prosthetic Heart Valve System" described in U.S. Patent Application Ser. No. 60/345,297 filed Jan. 2, 2003, all of which are incorporated herein by reference.

In one embodiment, the sizer body 14 is formed of at least one elastomeric material including, but not limited to, santoprene, silicon, and polyurethane. The annular wall 50 achieves a representative flexibility in a similar manner as described with respect to the outer ring 48. The representative flexibility of annular wall 50 is achieved by varying the material thickness, by increasing the durometer of the material, and/or by placing a stiffening element within an over-molded elastomeric material. Preferably, the annular wall 50 has a flexibility within 5% to 10% of the flexibility of the annular extension 47. In one embodiment, the annular wall 50 has a flexibility in the range of 90 to 110% of the annular extension 147.

Furthermore, since the outer ring 48 and the annular wall 50 each have a size and shape approximating the size and the shape of the sewing ring 34 and the stent 32, respectively, the overall size and shape of the sizer body 14 approximates the size and shape of the bioprosthetic heart valve 30. Similarly, since the annular wall 50 and the outer ring 48 each have different flexibilities representative of the first flexibility of the stent 34 and the second flexibility of the sewing ring 34, respectively, the overall sizer body 14 defines a variable flexibility. With this in mind, the variable flexibility of the sizer body 14 is representative of or substantially equal to the variable flexibility of the bioprosthetic heart valve 30.

Notably, although the sizer body 14 is representative of the bioprosthetic heart valve 30, it is not necessary for the sizer body 14 to include representations of the leaflets 36 as illustrated in FIG. 2B. However, in embodiments not illustrated, the sizer body 14 includes representations of the leaflets 36. The sizer body 14 is preferably sterilizable for reuse. In particular, the sizer body 14 is preferably formed such that the outer surfaces of the sizer body 14 are substantially continuous to promote the proper sterilization of the sizer body 14 between uses. In light of sterilization concerns, the sizer body 14 is formed without the cloth covers 44 and 46 (FIG. 2A) described above with respect to bioprosthetic heart valve 30.

Figure 2C:
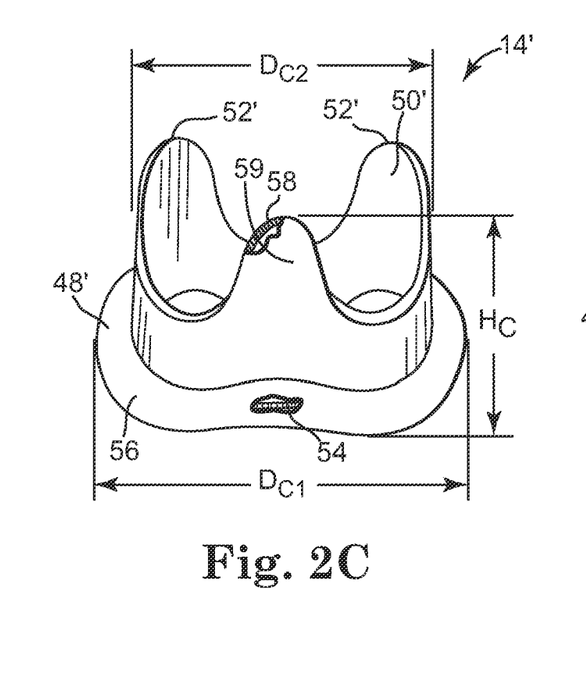
FIG. 2C is a perspective view of another embodiment of the flexible sizer body illustrated in FIG. 1.

An alternate embodiment of the sizer body 14' of the sizer assembly 10 (FIG. 1) corresponding to the exemplary bioprosthetic heart valve 30 of FIG. 2A is illustrated in FIG. 2C. The sizer body 14' includes an outer ring 48' and an annular wall 50'. The outer ring 48' is sized and shaped in a similar manner as the sewing ring 34 of the bioprosthetic heart valve 30. As such, the outer ring 48' has a circular or parabolic shape corresponding to the shape of the sewing ring 34. The outer ring 48' defines a maximum diameter $D_{C1}$ substantially equal to, i.e. within 1 mm of, the maximum sewing ring diameter $D_{A1}$ of the bioprosthetic heart valve 30. Furthermore, the outer ring 48' is formed with a flexibility representative of or approximating the flexibility of the sewing ring 34. In other words, the outer ring 48' has a substantially similar flexibility as the sewing ring 34. The representative flexibility of the outer ring 48' is achieved by forming the outer ring 48' to include a stiffening element 54 within an over-molded elastomeric material 56. The stiffening element 54 is preferably formed of a thin wire or contoured thermoplastic material, such as polypropylene, celcon, or acetyl homopolar. In one embodiment, the elastomeric material 56 is one of the group of, but not limited to, santoprene, silicon, and polyurethane.

The annular wall 50' extends from the outer ring 48', in a similar manner as the stent 32 and the stent posts 40 extend from the stent ring 38, terminating in rounded extremities or tips 52'. The annular wall 50' is sized and shaped in a similar manner as the stent 32 of the bioprosthetic heart valve 30. Therefore, with the embodiment of FIG. 2C, the sizer body 14 representing the heart valve 30, which has three of the stent posts 40, will similarly form three of the rounded extremities 52'. Alternatively, the annular wall 50' can form only two rounded extremities 52' to mimic a two stent post-type bioprosthetic heart valve (not shown).

Accordingly, the annular wall 50' extends from the outer ring 48' to produce an overall height $H_C$ of the sizer body 14' substantially equal to the overall height $H_A$ of the bioprosthetic heart valve 30. In particular, the overall height $H_C$ is within 1 mm of the overall height $H_A$. Further, the annular wall 50' defines a maximum wall diameter $D_{C2}$ substantially equal to the maximum stent diameter $D_{A2}$. Otherwise stated, the maximum wall diameter $D_{C2}$ is within 1 mm of the maximum stent diameter $D_{A2}$. The annular wall 50' has a flexibility similar to the flexibility of the annular extension 37. The representative flexibility of the annular wall 50' is achieved by forming the annular wall 50' to include a stiffening element 58 within an over-molded elastomeric material 59. In one embodiment, the stiffening element 58 is preferably formed of a thin wire or contoured thermoplastic material, such as polypropylene, celcon, or acetyl homopolar. The stiffening element 58 is formed of the same material having similar or different thicknesses or of a different material having similar or different thickness as the material of the stiffening element 54. In one embodiment, the elastomeric material 59 is one of the group of, but not limited to, santoprene, silicon, and polyurethane. The elastomeric material 59 can be formed at the same or at a different thickness as the elastomeric material 56. In one embodiment, the sizer body 14 (FIG. 2B) incorporates either the outer ring 48' or the annular wall 50'.

Figures 2D, 3:
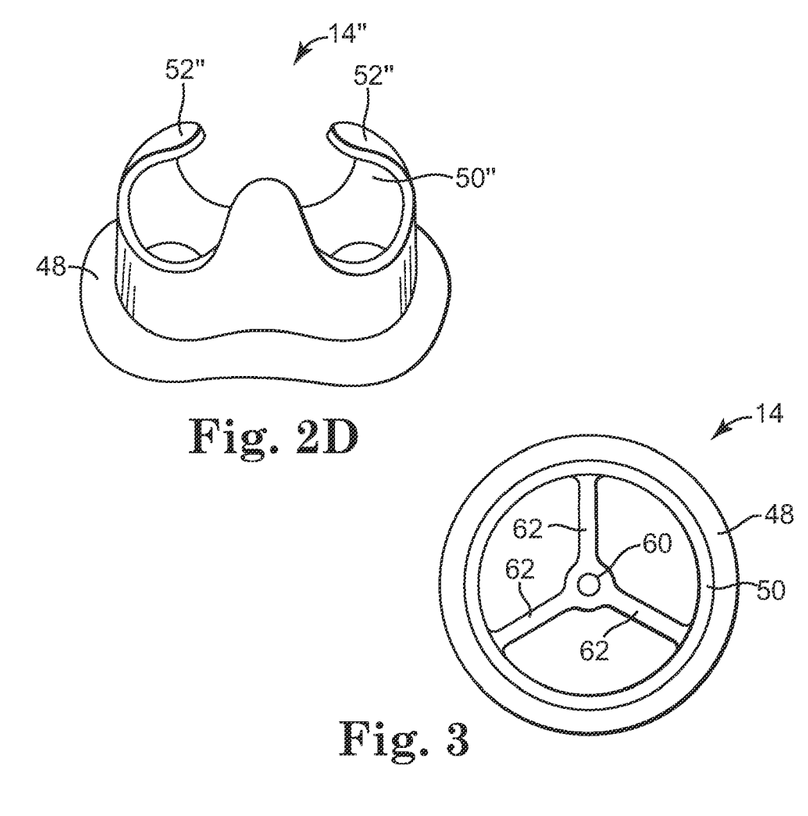
FIG. 2D is a perspective view of another embodiment of the flexible sizer body illustrated in FIG. 1.
FIG. 3 is a top view of one embodiment of the flexible sizer body illustrated in FIGS. 2B, 2C, and 2D.

Another alternate embodiment of the sizer body 14" of the sizer assembly 10 (FIG. 1) corresponding to the exemplary bioprosthetic heart valve 30 of FIG. 2A is illustrated in FIG. 2D. The sizer body 14" is similar to the sizer body 14 (FIG. 2B) in all respects other than those specifically described herein. The sizer body 14" includes an annular wall 50" similar to the annular wall 50 (FIG. 2B) having rounded extremities 52 (FIG. 2B). However, the rounded extremities 52" are permanently deflected inwardly an amount substantially similar to the amount in which the free ends 42 of the stent posts 40 deflect inwardly upon application of an external force of an insertion handle, which will be used in the subsequent implant procedure to position the bioprosthetic heart valve 30 within the patient (not shown). The permanent deflection of the rounded extremities 52" can be achieved through a variety of methods that will be apparent to one of skill in the art. In one embodiment, the rounded extremities 52" are constructed so as to assume the permanently deflected orientation of FIG. 2D such as by an internal frame component (e.g., the stiffening element 58 of FIG. 2C). In another embodiment, the annular wall 50" is formed to be inherently flexible (e.g., akin to the annular wall 50 of FIG. 2B), and thus selectively deflectable from a non-deflected orientation (e.g., akin to the orientation of FIG. 2B) to the deflected orientation of FIG. 2D by an external deflection device (not shown) otherwise coupled to the extremities 52".

With reference to FIG. 3, the sizer body 14 (or the sizer body 14' or 14") preferably further includes a handle reception area 60 to receive the connector 22 of the handle 12 (FIG. 1). The handle reception area 60 is sized and shaped to receive the connector 22 via a snap connection, a threaded connection, or any other biocompatible, selective or permanent coupling method. Preferably, the handle reception area 60 is substantially centered with respect to the outer ring 48 and the annular wall 50 to increase the ease of maneuverability of the sizer body 14 by the surgeon. In one embodiment, the handle reception area 60 is centered with respect to the annular wall 50 and the outer ring 48 by a plurality of spokes 62. Each of the plurality of spokes 62 is attached to and extends between the annular wall 50 and the handle reception area 60. The plurality of spokes 62 are circumferentially spaced around the handle reception area 60. In a preferred embodiment, the plurality of spokes 62 is limited in number to limit the obstruction of the surgeon's view through the sizer body 14 caused by each of the plurality of spokes 62. However, in other embodiments, the handle reception area 60 is attached to the annular wall 50 or the outer ring 48 via a solid, circumferential body.

With additional reference to FIG. 1, assembly of the sizer assembly 10 includes mating the connector 22 of the handle 12 with the handle reception area 60 of the sizer body 14. Although illustrated as a snap connection, in other embodiments the handle 12 is coupled with sizer body 14 in one of a plurality of fashions including a threaded attachment or any other spatially feasible, biocompatible attachment. In one embodiment, the handle 12 is selectively coupled with sizer body 14 such that the handle 12 can be selectively removed from the sizer body 14 and selectively coupled with other representative bodies (not illustrated). In an alternative embodiment, the handle 12 is permanently coupled with the sizer body 14.

Figure 4:
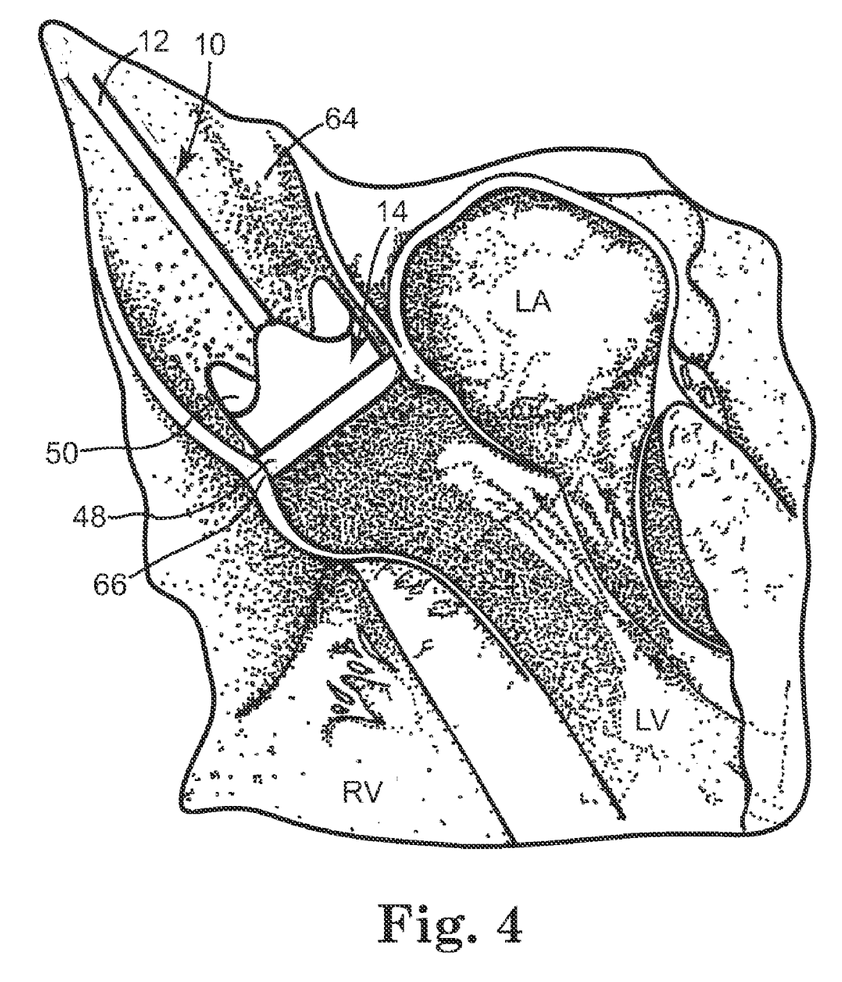
FIG. 4 is an illustration of the prosthetic heart valve sizer assembly being used during valve replacement surgery.

During heart valve replacement surgery, the surgeon will have a plurality of sizer assemblies 10 or at least a plurality of bodies 14 at his or her disposal. Each of the sizer assemblies 10, or more particularly each sizer body 14, corresponds with a different size or version of bioprosthetic heart valve 30 (an exemplary one of which is illustrated in FIG. 2A), i.e., is representative off or approximates the size, shape, and variable flexibility of an available bioprosthetic heart valve 30. The surgeon selects one of the plurality of sizer assemblies 10 or bodies 14 by grasping the grip portion 24 of the handle 12 and inserting the distal end 18 of the sizer assembly 10 into an aortic root 64 of a patient's heart valve annulus 66 as illustrated in FIG. 4.

The surgeon maneuvers the sizer assembly 10 to position the sizer body 14 above or within (dependent upon the implant technique being utilized) the heart valve annulus 66 to evaluate the fit of the selected sizer body 14. Since the sizer body 14 has a size, shape, and variable flexibility representative of the corresponding bioprosthetic heart valve 30, the sizer body 14 fits within and conforms to the structures within the aortic root 64 in a manner substantially similar to or substantially predictive of how the corresponding bioprosthetic heart valve 30 would fit within and conform to the structures within the aortic root 64. With this in mind, the surgeon compares the conformity of the outer ring 48 to the heart valve annulus 66 and evaluates the feasibility of subsequent suturing of the corresponding bioprosthetic heart valve 30 (illustrated in FIG. 2A) to the heart valve annulus 66. Furthermore, the surgeon observes and evaluates the positioning of the annular wall 50 within the aortic root 64 to ensure there is adequate space for the sizer body 14 and that the positioning of the annular wall 50 will not cause unintentional blockage. Preferably, the surgeon also evaluates the deflection of the annular wall 50 to determine if there is sufficient space between the annular wall 50 and the annulus 66 for accessing the outer ring 48 for suturing.

If the surgeon determines that the selected sizer assembly 10, or more particularly the selected sizer body 14, is a satisfactory and appropriate fit to the particular patient's heart valve annulus 66, he or she removes the sizer assembly 10 and selects the size and type of bioprosthetic heart valve 30 that corresponds with the sizer body 14 for subsequent implantation. However, if the surgeon determines that the sizer body 14 size or type is inappropriate for implantation to a patient's annulus 66, the sizer assembly 10 is removed and a different sized sizer body 14 or sizer assembly 10 is selected.

The newly selected sizer assembly 10 is inserted into the aortic root 64 of the patient and evaluated in a similar manner as described above with respect to the initially selected sizer assembly 10. This process is repeated until the performing surgeon determines the sizer body 14 of a selected sizer assembly 10 to be representative of the appropriate bioprosthetic heart valve 30. At such a time, the sizer assembly 10 is removed, and a bioprosthetic heart valve 30, which corresponds to the sizer body 14 determined to be appropriate by the surgeon, is selected. Notably, although described and illustrated for use with an aortic valve, a heart valve sizer can be used during heart valve replacement of any of the valves (i.e., mitral valve, tricuspid valve, aortic valve, and pulmonary valve).

In one embodiment, not only is the size and flexibility of the sizer body 14 analyzed within the aortic root 64 of the patient, but the implantation technique is also evaluated. In particular, a surgeon uses a selected sizer body 14 and evaluates the sizer body 14 in both a super-annular and an intra-annular position. This evaluation allows the surgeon to observe whether a particular size of the sizer body 14 is more aptly suited for implantation via the super-annular or intra-annular implantation technique. In particular, the surgeon evaluates the size of the outer ring 48 and the annular wall 50 with respect to the annulus 66 and an annulus opening 68 as well as the flexible conformity of the outer ring 48 to the annulus 66 and the annular wall 50 within the aortic root 64 in both positions. Such observation allows the surgeon to determine which implantation technique would more beneficially suit the particular patient undergoing the heart valve replacement surgery.

Figure 5:
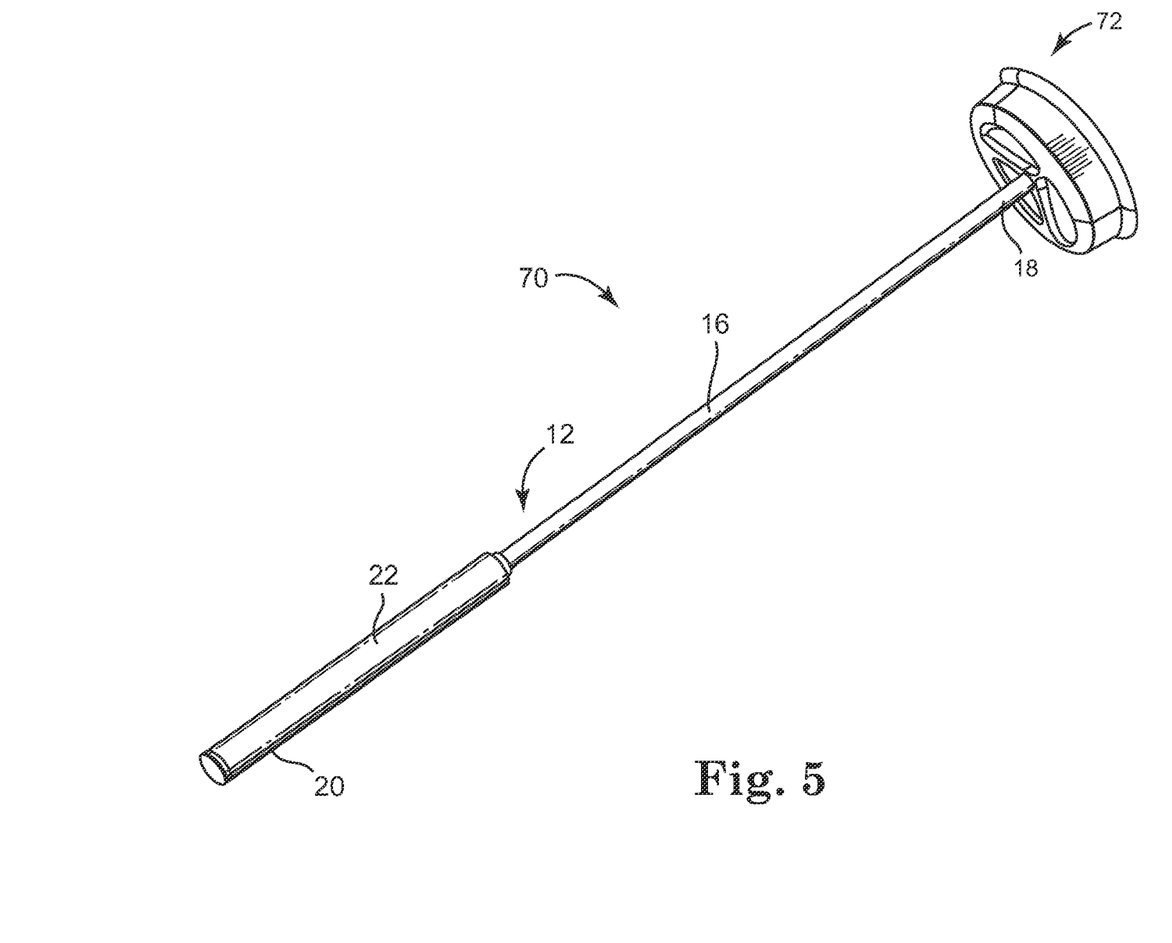
FIG. 5 is a perspective view of another embodiment prosthetic heart valve sizer assembly including a flexible sizer body in accordance with the present invention.

An alternative embodiment prosthetic heart valve sizer 70 is generally illustrated in FIG. 5. Heart valve sizer 70 includes the handle 12 and a sizer body 72. The handle 12 is similar to the handle 12 described with respect to the sizer assembly 10 (FIG. 1). The sizer body 72 is representative of a mechanical heart valve 74 illustrated in FIG. 6A. In a similar manner as described above with respect to the sizer assembly 10, the distal end 18 of the handle 12 is permanently or selectively coupled to the sizer body 72.

Figure 6A:
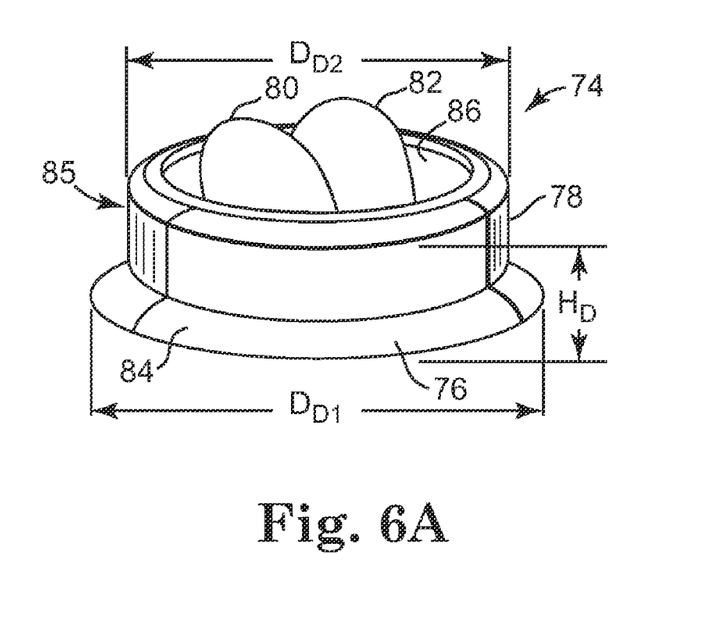
FIG. 6A is a perspective view of one embodiment of a mechanical prosthetic heart valve corresponding to the flexible sizer body illustrated in FIG. 5.

Referring to FIG. 6A, the mechanical heart valve 74 typically includes a sewing ring 76, an annular housing 78, and rigid leaflets 80 and 82. The sewing ring 76 is formed by a flexible and biocompatible cloth 84 which may or may not be filled with biocompatible filler and typically defines a circular or parabolic shape. The annular housing 78 is coupled with and extends from the sewing ring 76. In general, the annular housing 78 forms an annular extension 85. The rigid leaflets 80 and 82 have pivots (not shown) that rotatably engage an interior surface 86 of the annular housing 78. Both the housing 78 and the rigid leaflets 80 and 82 are made of a relatively rigid and biocompatible material. Since the sewing ring 76 and the housing 78 each define or possess a different level of flexibility, the overall mechanical heart valve 74 accordingly defines a variable flexibility.

During use, the mechanical heart valve 74 is attached to a valve annulus (not shown) via the sewing ring 76. With this in mind, the mechanical heart valve 74 is available in a plurality of sizes corresponding to the plurality of sizes of heart valve annuli and valve openings of heart valve replacement patients. As such, each size of the mechanical heart valve 74 has a maximum sewing ring diameter $D_{D1}$ and a housing diameter $D_{D2}$. In addition, the mechanical heart valve 74 has an overall height HD as defined by the annular housing 78 and the sewing ring 76.

Figure 6B:
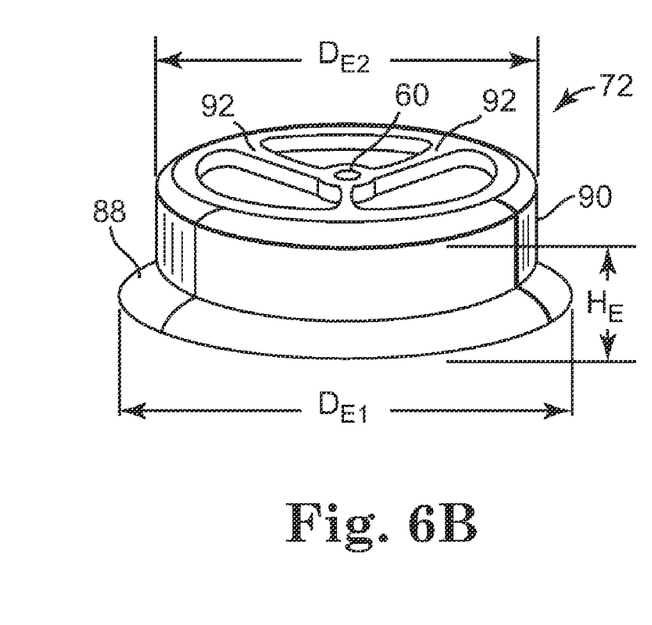
FIG. 6B is a perspective view of one embodiment of the flexible sizer body illustrated in FIG. 5.

As illustrated in FIGS. 6A and 6B, the sizer body 72 is representative of the mechanical heart valve 74. As such, the sizer body 72 includes an outer ring 88 and an annular wall 90. The outer ring 88 is sized and shaped in a manner similar as described with respect to the sewing ring 76. Therefore, the outer ring 88 is circular or parabolic depending upon the shape of the sewing ring 76 of the mechanical heart valve 74 being represented. As such, the sizer body 72 defines an outer ring maximum diameter $D_{E1}$ that is substantially equal to, i.e. within 1 mm of, the maximum sewing ring diameter $D_{D1}$ of the mechanical heart valve 74. In addition, the outer ring 88 has a flexibility representative of the flexibility of the sewing ring 76. Preferably, the outer ring 88 has a flexibility within 5% to 10% of the flexibility of the sewing ring 76. In one embodiment, the outer ring 88 has a flexibility in the range of 90 to 110% of the sewing ring 76. The representative flexibility of the outer ring 88 is achieved in a similar manner as described above with respect to the outer ring 48 (FIG. 2B).

The annular wall 90 extends from the outer ring 88 in a similar manner as the annular housing 78 extends from the sewing ring 76. As such, the annular wall 90 has a similar size and shape as the annular housing 78. In particular, the annular wall 90 defines a maximum wall diameter $D_{E2}$ that is substantially equal to, i.e. within 1 mm of, the maximum annular housing diameter $D_{D2}$ of the mechanical heart valve 74. Furthermore, the sizer body 72 defines an overall height $H_E$ substantially equal to, i.e., within 1 mm of, the overall height HD of the mechanical heart valve 74. In addition, the annular wall 90 has a flexibility representative of the flexibility of annular extension 85. Preferably, the annular wall 90 has a flexibility within 5% to 10% of the flexibility of the annular extension 85. In one embodiment, the annular wall 90 each have a flexibility in the range of 90 to 110% of the annular extension 85. The representative flexibility of the annular wall 90 is achieved in a similar manner as described above with respect to the annular wall 50 (FIG. 2B).

Notably, since the outer ring 88 and the annular wall 90 each have a different flexibility representative of the different flexibilities of the sewing ring 76 and the annular extension 85, respectively, the overall sizer body 72 defines a variable flexibility representative of the variable flexibility of the mechanical heart valve 74. Furthermore, the size and the shape of the overall sizer body 72 are representative of the overall size and shape of the mechanical heart valve 74. In one embodiment, the sizer body 72 is formed of at least one elastomeric material including, but not limited to, santoprene, silicon, and polyurethane. The sizer body 72 is preferably sterilizable for reuse. In particular, the sizer body 72 is preferably formed such that the outer surfaces of the sizer body 72 are substantially continuous to promote proper sterilization of the sizer body 72 between uses.

The sizer body 72 further includes the handle reception area 60, which is similar to the handle reception area 60 described with respect to the sizer assembly 10. The handle reception area 60 is preferably centered with respect to the annular wall 90. In one embodiment, the handle reception area 60 is connected to the annular wall 90 via a plurality of spokes 92 circumferentially spaced around the annular wall 90. Each of the plurality of spokes 92 extends between and couples the annular wall 90 to the handle reception area 60. As such, the sizer body 72 is attached to handle 12 (FIG. 5) via the handle reception area 60 in any of the manners described above with respect to the sizer body 14 (FIG. 1).

Notably, although the sizer body 72 is representative of the mechanical heart valve 74, it is not necessary for the sizer body 72 to include representations of the rigid leaflets 80 and 82 as illustrated in FIG. 6B. However, in embodiments not illustrated, the sizer body 72 includes valve representations of the rigid valves 80 and 82. The heart valve sizer 70, and more particularly the sizer body 72, is used during heart valve replacement surgery in a similar manner as described above with respect to the sizer assembly 10, and more particularly the sizer body 14.

Figure 7:
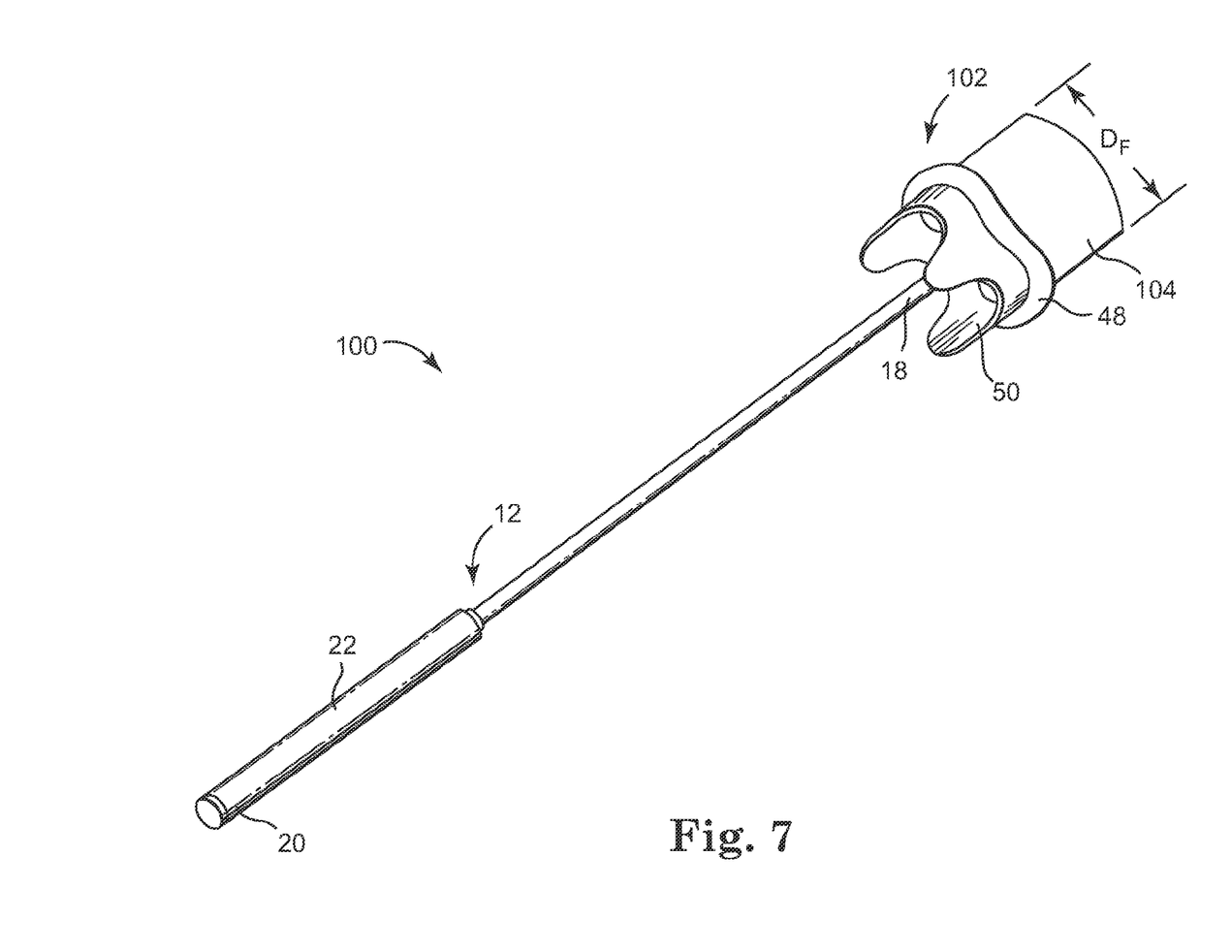
FIG. 7 is a perspective view of an alternative embodiment prosthetic heart valve sizer assembly including a flexible sizer body in accordance with the present invention.

FIG. 7 illustrates yet another embodiment of a prosthetic heart valve sizer assembly generally illustrated at 100. The sizer assembly 100 includes the handle 12 and a body 102. The handle 12 is similar to the handle 12 described with respect to the sizer assembly 10. The distal end 18 of the handle 12 is connected to the sizer body 102. The sizer body 102 includes the sizer body 14 described above. In addition, a traditional cylinder sizer 104 extends form the sizer body 14.

The cylinder sizer 104 extends distally from the outer ring 48 in a direction opposite that of the annular wall 50. The cylinder sizer 104 is typically used to determine the diameter of the valve opening within a patient undergoing heart valve replacement surgery. As such, the particular cylinder sizer 104 placement with respect to the outer ring 48 is dependent upon the surgical technique being utilized. In particular, for an intra-annular implant technique, the cylinder has a diameter $D_F$ substantially equal to, i.e., within 1 mm of, the outer ring diameter of $D_{B1}$. Conversely, for a supra-annular implant technique, the cylinder sizer 104 has a diameter $D_F$ more nearly representative of the annular wall diameter $D_{B2}$ (FIG. 2B). The combination of the cylinder sizer 104 with the outer ring 48 and the annular wall 50 allows a surgeon to utilize prior art sizing techniques along with the sizing techniques of the present invention. Notably, although the sizer assembly 100 is illustrated with the sizer body 14 representative of a bioprosthetic heart valve 30 (FIG. 2A), the sizer assembly 100 incorporating a cylinder sizer 104 can also be incorporated in a sizer representative of the mechanical heart valve 74 (FIG. 6A).

Figure 8:
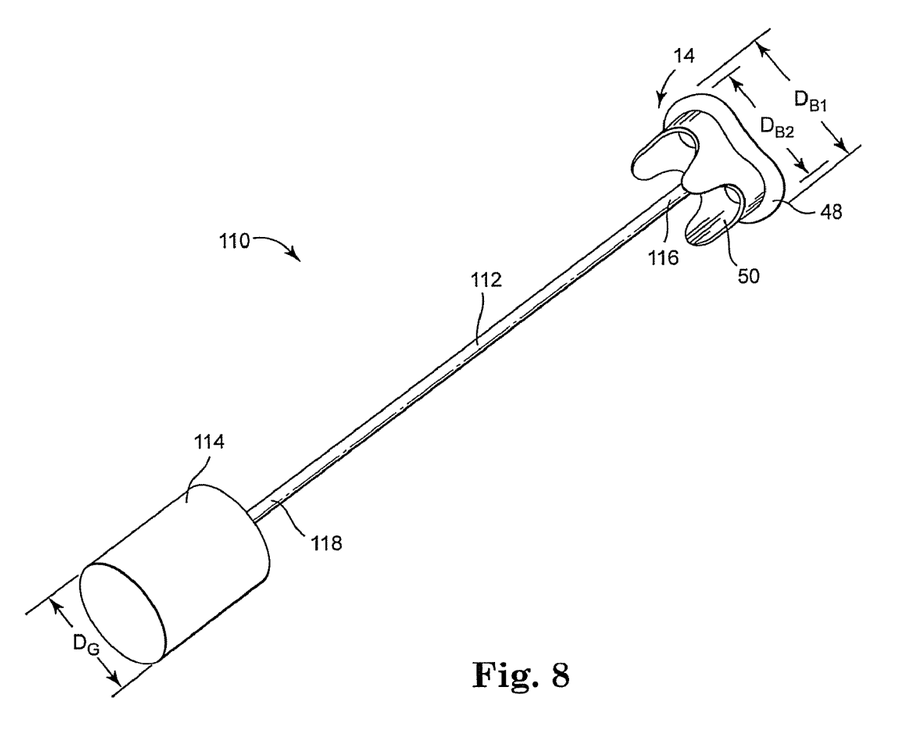
FIG. 8 is a perspective view of an alternative embodiment prosthetic heart valve sizer assembly including a flexible sizer body in accordance with the present invention.

Another alternative embodiment of a prosthetic heart valve sizer assembly 110 is generally illustrated in FIG. 8. The sizer assembly 110 includes a handle 112, the sizer body 14, similar to the sizer body 14 described above with respect to the sizer assembly 10 (FIG. 1), and a traditional cylinder sizer 114. The handle 112 is similar to the handle 12 (FIG. 1) described above with respect to the sizer assembly 10 except for those features specifically described herein. The handle 112 defines a first end 116 and a second end 118. The first end 116 is coupled with the sizer body 14 in a similar manner as described with respect to the handle 12. The traditional cylinder sizer 114 is coupled with and substantially centered on the second end 118 of the handle 112. The cylinder sizer 114 is coupled with the handle 112 via a snap connection, a threaded connection, or any other spatially feasible and biocompatible method of attachment. Similar to prior art sizers, the cylinder sizer 114 defines a diameter $D_G$ used to size the valve opening 68 (illustrated in FIG. 4) in the patient undergoing prosthetic heart valve replacement. As such, for an intra-annular implant technique, the diameter $D_G$ of the cylinder 114 is substantially equal to the outer ring diameter $D_{B1}$ of the sizer body 14. Similarly, a sizer assembly 110 used for a supra-annular implant technique includes the cylinder sizer 114 in which the diameter $D_G$ is substantially equal to, i.e., within 1 mm of, the wall diameter $D_{B2}$ of the sizer body 14.

During use of the sizer assembly 110, the sizer assembly 110 is placed within the aortic root 64 (FIG. 4) of a patient with the cylinder sizer 114 as the leading (or distal) end. The cylinder sizer 114 is used by the surgeon to measure the diameter of the heart valve annulus opening 68. During surgery, the surgeon typically has a number of sizes of the sizer assembly 110 available. The surgeon systemically inserts the differently sized sizer assembly 110 until the cylinder sizer 114 of the currently inserted or selected sizer assembly 110 corresponds with the size of the particular patient's heart valve opening 68.

Upon determining the proper size of the heart valve opening 68, the surgeon removes the sizer assembly 110 from the aortic root 64 and subsequently replaces the sizer assembly 110 into the aortic root 64 with the sizer body 14 as the leading (or distal) end. Upon insertion of the sizer assembly 110, in particular the sizer body 14, the surgeon further evaluates the fit of the sizer body 14 including the size and flexibility of the outer ring 48 and the annular wall 50. Once again it is noted that since the sizer body 14 has a size, shape, and variable flexibility representative of the corresponding bioprosthetic heart valve 30, the sizer body 14 fits within and conforms to the structures within the aortic root 64 in a manner substantially similar to or substantially predictive of how the corresponding bioprosthetic heart valve 30 would fit within and conform to the structures within the aortic root 64. Therefore, upon determination that the sizer body 14 is an appropriate fit to the patient's annulus opening 68, the surgeon selects a bioprosthetic heart valve 30 corresponding to the sizer assembly 110 for implantation.

If the surgeon determines that the body 114 inserted into the patient is inadequate for size or flexibility reasons, he or she removes the sizer assembly 110 and replaces it with a second sizer assembly 110 having a slightly different sized sizer body 14 and repeats the process until a sizer assembly 110 is found with a sizer body 14 that most nearly corresponds to the patients heart valve annulus 66. Upon selection of a sizer body 14 that most nearly corresponds to the patient's heart valve annulus 66, the sizer assembly 110 is removed and a bioprosthetic heart valve 30 is selected that corresponds to the selected sizer assembly 110. Notably, although the sizer assembly 110 is illustrated with a sizer body 14, which is representative of the bioprosthetic heart valve 30, in one alternative embodiment the sizer assembly 110 instead incorporates a sizer body 72 representative of the mechanical heart valve 74.

In general, the heart valve sizer in accordance with the present disclosure includes a body with a shape, a size, and a variable flexibility representative of or substantially similar to an available heart valve prosthesis, such as a bioprosthetic heart valve or mechanical heart valve. These characteristics of the sizer allows a surgeon to not only evaluate the size of an annulus opening but also to evaluate the overall fit and conformity of a particular prosthesis to an annulus and/or within a patient's annulus opening. The evaluation of the representative body within the aortic root provides the surgeon with additional knowledge, thereby, allowing he or she to select a heart valve prosthesis and/or method of implantation that is more likely to fit and more suitable to the heart annulus of the particular patient. The added certainty concerning the size of the prosthesis and method of implantation not only prevents waste of discarded prostheses but also saves time during the heart valve replacement surgery, thereby benefiting the overall prognosis of the patient.

Although the present disclosure has been described with reference to preferred embodiments, workers skilled in the art will recognize that changes can be made in form and detail without departing from the spirit and scope of the present invention.

What is claimed is:

1. A method for evaluating a valve annulus to determine a proper size of a prosthetic heart valve to be sewn to the valve annulus during heart valve replacement surgery, the method comprising:
   providing a first prosthetic heart valve including:
      an annular extension having a first flexibility, and
      a sewing ring having a second flexibility differing from the first flexibility,
   providing a first flexible sizer body including:
      an outer ring corresponding with the sewing ring, and
      an annular wall coupled to and extending from the outer ring, the annular wall corresponding with the annular extension and having a flexibility substantially similar to the first flexibility of the annular extension of the first prosthetic heart valve, the annular wall forming a plurality of extremities adapted to be inwardly deflected;
   inserting the first flexible sizer body into an opening of the heart valve annulus to determine whether the first flexible sizer body properly fits and conforms with the heart valve annulus;
   evaluating whether the first prosthetic heart valve is appropriate for implanting to the heart valve annulus based upon the determination of whether the first flexible sizer body properly fit and conformed to the heart valve annulus; and
   evaluating deflection of the plurality of extremities to determine a spacing between the annular wall and the heart valve annulus for accessing the outer ring.

2. The method of claim 1, further comprising:
   providing a plurality of additional flexible sizer bodies, respective ones of which differ from one another in terms of at least one of size and shape,
   selectively inserting respective ones of the plurality of additional flexible sizer body into the opening of the heart valve annulus for a plurality of differently configured flexible sizer bodies until one of the flexible sizer bodies is determined to fit and conform to the heart valve annulus.

3. The method of claim 2, wherein each of the plurality of additional flexible sizer bodies corresponds to a differently sized prosthetic heart valve.

4. The method of claim 2, wherein each of the plurality of additional flexible sizer bodies corresponds to a different implantation technique.

5. The method of claim 1, further comprising:
   determining whether the first flexible sizer body is more suitable to interact with the heart valve annulus in an intra-annular or a supra-annular position.

6. The method of claim 5, further comprising:
   performing a heart valve replacement surgery utilizing an implantation technique selected from the group of an intra-annular technique and a supra-annular technique, wherein the implantation technique is selected based upon a determination of which position of the first flexible sizer body with respect to the heart valve annulus is more suitable for a particular patient.

7. The method of claim 1, wherein the outer ring of the first flexible sizer body has a flexibility substantially similar to the second flexibility of the first prosthetic heart valve.

8. The method of claim 7, wherein the flexibility of the annular wall of the first flexible sizer body is 90%-110% of the first flexibility of the first prosthetic heart valve.

9. The method of claim 8, wherein the flexibility of the outer ring of the first flexible sizer body is 90%-110% of the second flexibility of the first prosthetic heart valve.

10. The method of claim 9, wherein a size and shape of the outer ring of the first flexible sizer body corresponds with a size and shape of the sewing ring of the first prosthetic heart valve.

11. The method of claim 10, wherein a size and shape of the annular wall of the first flexible sizer body corresponds with a size and shape of the annular extension of the first prosthetic heart valve.

12. The method of claim 11, further comprising:
   providing a second prosthetic heart valve including a sewing ring and an annular wall;
   providing a second flexible sizer body including an outer ring, corresponding in shape, size, and flexibility with the sewing ring of the second prosthetic heart valve, and an annular wall, corresponding in shape, size, and flexibility with the annular extension of the second prosthetic heart valve;
   wherein the first and second prosthetic heart valves differ by at least one of size and shape.

13. The method of claim 12, further comprising:
   providing a handle;
   attaching the first flexible sizer body to the handle;
   inserting the first flexible sizer body into the opening of the heart valve annulus by manipulating the handle;
   detaching the first flexible sizer body from the handle;
   attaching the second flexible sizer body to the handle; and
   inserting the second flexible sizer body into the opening of the heart valve annulus by manipulating the handle.

14. The method of claim 1, further comprising:
   surgically removing native valve leaflets associated with the heart valve annulus prior to inserting the first flexible sizer body.

15. The method of claim 1, wherein an overall height of the first flexible sizer body is substantially equivalent to an overall height of the first prosthetic heart valve.

16. A method for evaluating a valve annulus to determine a proper size of a prosthetic heart valve to be sewn to the valve annulus during heart valve replacement surgery, the method comprising:

providing a first prosthetic heart valve including:
an annular extension having a first flexibility, and
a sewing ring having a second flexibility differing from the first flexibility,
wherein the annular extension of the first prosthetic heart valve includes a plurality of inwardly deflectable stent posts, the first prosthetic heart valve configured to be implanted in a deflected state in which the stent posts are held in an inwardly deflected position, providing a first flexible sizer body including:
an outer ring corresponding with the sewing ring, and
an annular wall coupled to and extending from the outer ring, the annular wall corresponding with the annular extension and having a flexibility substantially similar to the first flexibility of the annular extension of the first prosthetic heart valve,
wherein providing the first flexible sizer body further includes forming the annular wall to define a plurality of extremities commensurate with the deflected state of the first prosthetic heart valve;

inserting the first flexible sizer body into an opening of the heart valve annulus to determine whether the first flexible sizer body properly fits and conforms with the heart valve annulus; and evaluating whether the first prosthetic heart valve is appropriate for implanting to the heart valve annulus based upon the determination of whether the first flexible sizer body properly fit and conformed to the heart valve annulus.

* * * * *